United States Patent
Mueller et al.

(10) Patent No.: US 9,562,869 B2
(45) Date of Patent: Feb. 7, 2017

(54) PORTABLE ELECTRONIC DEVICE

(71) Applicant: Sensirion AG, Stafa (CH)

(72) Inventors: Martin Mueller, Zurich (CH);
Dominik Niederberger, Zurich (CH);
Dominic Boni, Dielsdorf (CH)

(73) Assignee: Sensirion AG, Stafa (CH)

( * ) Notice: Subject to any disclaimer, the term of this patent is extended or adjusted under 35 U.S.C. 154(b) by 49 days.

(21) Appl. No.: 14/620,658

(22) Filed: Feb. 12, 2015

(65) Prior Publication Data

US 2015/0241370 A1    Aug. 27, 2015

(30) Foreign Application Priority Data

Feb. 25, 2014    (EP) .................................... 14000666

(51) Int. Cl.
| | |
|---|---|
| G06F 3/0488 | (2013.01) |
| G01N 25/66 | (2006.01) |
| G01K 1/20 | (2006.01) |
| G06F 3/041 | (2006.01) |
| H04M 1/725 | (2006.01) |
| H04M 1/18 | (2006.01) |

(52) U.S. Cl.
CPC ................. *G01N 25/66* (2013.01); *G01K 1/20* (2013.01); *G06F 3/0418* (2013.01); *H04M 1/72522* (2013.01); *H04M 1/18* (2013.01); *H04M 2250/12* (2013.01)

(58) Field of Classification Search
CPC ........ G06F 3/0488; G06F 3/044; G06F 3/045; G06F 11/3058
See application file for complete search history.

(56) References Cited

U.S. PATENT DOCUMENTS

| | | | |
|---|---|---|---|
| 3,817,453 | A | 6/1974 | Pinckaers |
| 4,096,575 | A | 6/1978 | Itoh |
| 5,199,637 | A | 4/1993 | Adams |
| 5,502,838 | A | 3/1996 | Kikinis |
| 5,721,837 | A | 2/1998 | Kikinis et al. |
| 6,912,386 | B1 | 6/2005 | Himberg et al. |
| 7,027,834 | B2 | 4/2006 | Soini et al. |
| 7,280,301 | B1 | 10/2007 | Jackson et al. |
| 7,364,353 | B2 | 4/2008 | Kolk |

(Continued)

FOREIGN PATENT DOCUMENTS

| | | |
|---|---|---|
| EP | 0387025 | 3/1989 |
| EP | 1469323 | 10/2004 |

(Continued)

OTHER PUBLICATIONS

European Search Report Number For European Application No. 14000666.9-1559, dated Jul. 15, 2014.

(Continued)

*Primary Examiner* — Ricardo L Osorio

(74) *Attorney, Agent, or Firm* — Cooper & Dunham LLP

(57) ABSTRACT

In a portable electronic device, an ambient temperature is sensed by means of a temperature sensor. In addition, it is assessed if the portable electronic device is exposed to condensation. A corresponding condensation indicator is provided. The condensation indicator is determined based on a dew point and based on sensed temperature values of the past or temperature derived from the past sensed temperature values.

20 Claims, 2 Drawing Sheets

(56) References Cited

U.S. PATENT DOCUMENTS

| | | | |
|---|---|---|---|
| 9,366,584 B2* | 6/2016 | Graf | G01K 1/20 |
| 2003/0064749 A1 | 4/2003 | Soini et al. | |
| 2006/0025897 A1* | 2/2006 | Shostak | B60C 23/005 701/1 |
| 2006/0046038 A1* | 3/2006 | Nakanishi | B32B 7/14 428/212 |
| 2009/0139781 A1* | 6/2009 | Straubel | B60L 11/1875 180/65.1 |
| 2009/0140059 A1 | 6/2009 | Barton et al. | |
| 2009/0144014 A1 | 6/2009 | Aljabari | |
| 2010/0123675 A1* | 5/2010 | Ippel | G06F 3/044 345/173 |
| 2010/0163713 A1 | 7/2010 | Cheng et al. | |
| 2011/0059775 A1 | 3/2011 | Choi et al. | |
| 2011/0119018 A1 | 5/2011 | Skarp | |
| 2011/0127026 A1 | 6/2011 | Schuch et al. | |
| 2011/0216806 A1 | 9/2011 | Weng | |
| 2011/0307208 A1 | 12/2011 | Graf et al. | |
| 2012/0127520 A1* | 5/2012 | Shimao | G06F 3/0418 358/1.15 |
| 2012/0253691 A1 | 10/2012 | Graf et al. | |
| 2013/0088429 A1* | 4/2013 | Yang | G06F 1/3231 345/158 |
| 2013/0100037 A1* | 4/2013 | Mabie | G06F 3/0418 345/173 |
| 2014/0355649 A1 | 12/2014 | Niederberger et al. | |

FOREIGN PATENT DOCUMENTS

| | | |
|---|---|---|
| EP | 1873506 | 1/2008 |
| EP | 1947432 | 7/2008 |
| EP | 2682715 | 1/2014 |
| GB | 2190203 | 11/1987 |
| JP | 2010101741 | 5/2010 |
| WO | 0169341 | 9/2001 |
| WO | 2012027754 | 3/2012 |
| WO | 2014005235 | 1/2014 |

OTHER PUBLICATIONS

Sensirion, "Humidity at a Glance Most Relevant Equations with Sample Code", Version, 1.0, pp. 1-2, Aug. 2008.

Sensirion, "Introduction to Humidity" Basic Principles on Physics of Water Vapor, Version 2.0, Aug. 2009, pp. 1-6.

Steven W. Smith, The Scientists and Engineer's Guide to Digital Signal Processing, "Statistics, Probability and Noise", Chapter 2, pp. 11-34, Apr. 27, 2006.

Mayank Goel et al.. "GripSense: Using Built in Sensors to Detect Hand Posture and Pressure on Commodity Mobile Phones", UIST 12, Oct. 7-10, 2012, Cambridge, MA, USA, pp. 545-554.

Sensirion, Datasheet STS21 Temperature Sensor IC, Version 2, Dec. 2011, pp. 1-12.

Sensirion, Datasheet SHT C1 Humidity and Temperature Sensor IC, Version 3, May 2014, pp. 1-14.

* cited by examiner

PORTABLE ELECTRONIC DEVICE

CROSS REFERENCES TO RELATED APPLICATIONS

This application claims the priority of European patent application 14 000 666.9, filed Feb. 25, 2014, the disclosure of which is incorporated herein by reference in its entirety.

TECHNICAL FIELD

The present invention relates to a portable electronic device, to a method for operating a portable electronic device, and to a computer program element for operating a portable electronic device.

BACKGROUND ART

Portable electronic devices such as smartphones, for example, may contain one or more sensors which may be impacted in their operation subject to environmental conditions.

DISCLOSURE OF THE INVENTION

According to a first aspect of the present invention, a portable electronic device is provided. In case of the device being exposed to condensation, a condensate having deposited on the device as a result of the condensation process may impact a measurement, e.g. a measurement of ambient temperature, or a measurement of the capacitance of a touchscreen of the device. Condensation may occur, for example, when moving the device to a warmer and more humid environment. In view of a lower temperature of the device relative thereto, the humid air may start building a film of water on the device. During this process, latent heat is released during the process of condensation and acts as a heat input to the device. Over time, the temperature of the device approximates the ambient temperature and the condensate may evaporate again, wherein the heat bound in the condensate is released.

Hence, in case it is desired to sense the ambient temperature, for example, a temperature value may be sensed that does not correspond to a real value of the ambient temperature but rather deviates therefrom owed to the heating effect of condensation, or later on, owed to the cooling effect of evaporation. In case the device contains a touchscreen, the condensate may impact the input functionality. Hence, it is desired to compensate for one or more of such effects.

For this purpose, a condensation assessment module is provided in the portable electronic device which takes an assessment as to if the portable electronic device is exposed to condensation. The condensation assessment module assesses the occurrence of condensation by determining a dew point temperature. Condensation typically occurs, when the dew point of the environment exceeds a temperature of an object/device that becomes exposed to this environment. Hence, it is preferred that the condensation assessment module is configured to determine the dew point temperature—in short dew point. The portable electronic device comprises a temperature sensor for sensing an ambient temperature. The temperature sensor preferably provides a sufficient coupling to the environment of the portable electronic device, e.g. by being exposed to the ambient through openings in a housing of the device or other means. The sensed temperature value or a temperature value derived therefrom may be used for determining the dew point. Preferably, the dew point is compared to a temperature of the device. The temperature of the device may be represented by a temperature sensed in the past by the temperature sensor in view of the temperature of the device being rather inert to external changes. For this purpose, one or more temperature values sensed in the past may be recorded in a storage or memory of the device and be used for a comparison with the dew point. In an alternate embodiment, instead of the past sensed temperature values, one or more of temperature values may be derived from the past sensed temperature values and be applied to the comparison with the dew point. The one or more past derived temperature values may instead of the past sensed temperature values or in addition be stored in the storage or memory of the device. In a preferred embodiment, the dew point may be compared to one past sensed or one past derived temperature value, or to multiple past sensed or to multiple past derived temperature values. Condensation may be confirmed in case the dew point exceeds the one past sensed or one past temperature value in the first alternative, or each of the multiple past sensed or each of the multiple past derived temperature values in the second alternative.

In another embodiment, it is rather an average or a weighted temperature value derived from multiple past sensed or past derived temperature values that is used in the comparison with the dew point. This may provide an even better assessment. Hence, in such embodiments, the dew point may be compared to an average sensed temperature value or to a weighted sensed temperature value, or to an average derived temperature value or to a weighted derived temperature value.

While according to one of the above embodiments condensation may be confirmed in case of the dew point exceeding the subject temperature value/s representing a temperature of the device, in another embodiment, a given margin is to be exceeded between the dew point and the subject temperature value/s for confirming condensation, or, in another embodiment, the dew point may be allowed to be equal or more than the subject temperature value/s for confirming condensation. It is understood, that only the embodiment actually used for the condensation assessment needs to be implemented in the condensation assessment module, which preferably is a software module.

It is preferred, that the sensed temperature value or the derived temperature value is used in the determination of the dew point. It is further preferred, that the portable electronic device comprises a humidity sensor which provides a humidity value which preferably is used for determining the dew point, preferably together with the sensed or derived temperature value. Hence, it is preferred that the present sensed or derived temperature value and the present humidity value are used for determining the dew point. Preferably, the humidity sensor may be integrated on the same chip as the temperature sensor. The condensation assessment module is configured to determine the dew point at least dependent on a humidity value sensed by the humidity sensor and dependent on the sensed temperature value or the derived temperature value. The humidity value preferably is a relative humidity value, and in one embodiment, the determination of the dew point F may follow:

$$F(RH, T_S) = T_n \frac{\ln\left(\frac{RH \exp^{\frac{mT_S}{T_n + T_S}}}{100\%}\right)}{m - \ln\left(\frac{RH \exp^{\frac{mT_S}{T_n + T_S}}}{100\%}\right)}$$

wherein:

F denotes the dew point in ° Celsius,

RH denotes the relative humidity in %, $T_s$ denotes the sensed temperature in ° Celsius, m denotes a first constant, and $T_n$ denotes a second constant.

This formula for the dew point is derived from the Magnus formula. The constant m may be set to 17.62, while the constant $T_n$ may be set to 243.120 Celsius. With these constants m, $T_n$ the dew point F remains dependent from the relative humidity RH and the temperature $T_s$, wherein the relative humidity RH itself is dependent from the temperature $T_s$, i.e. $RH=f(T_s)$. Note that the relative humidity RH is rising when the temperature $T_s$ is falling, and vice versa. Other approximations to determining the dew point and/or the underlying saturation vapour pressure may be used instead, or in addition to the above approximation.

In case the dew point is determined based on the sensed temperature value, such dew point preferably is compared to one or more sensed temperature values of the past, or to an averaged or weighed sensed temperature value built from the sensed temperature values of the past. In case the dew point is determined based on a derived temperature value which in one embodiment may be a compensated temperature value as will be explained later on—wherein in the above formula the sensed temperature $T_s$ may be replaced by the derived temperature $T_A$—, such dew point preferably is compared to one or more derived temperature values of the past, or to an averaged or weighed derived temperature value built from the derived temperature values of the past.

It is preferred, that the condensation assessment module supplies information as to the result of its assessment in form of a condensation indicator, which condensation indicator may in a first approach represent any form of data indicating at least either the presence or absence of condensation, and in a variant even a degree of condensation. Preferably, the condensation indicator is a binary indicator indicating either a presence of condensation or an absence of condensation. The condensation indicator may specifically be used in a compensator as an indicator if a compensation for condensation is required or not, and possibly to which degree such compensation may be required.

In a preferred embodiment, the ambient temperature sensor not only is provided for determining the dew point, but also for determining an ambient temperature. A condensate having deposited on the device as a result of a condensation process may impact the measurement of the ambient temperature. For compensating for the impact of condensation, it is preferred that a compensator is provided in the portable electronic device. The compensator is designed for compensating for a deviation of a value of the ambient temperature sensed by the temperature sensor from a real value of the ambient temperature which deviation is at least owed to condensation. The compensator provides a compensated temperature value for the ambient temperature which compensated temperature value is desired to come more close to the real value of the ambient temperature than the sensed temperature value, or even match it. Hence, the compensator is configured to determine a compensated value for the ambient temperature at least dependent on the sensed temperature value and dependent on the condensation indicator provided by the condensation assessment module.

In a preferred embodiment, the detection of condensation may lead in the compensator to applying a condensation compensation value directly to the sensed temperature value in order to approximate the real temperature value. Such condensation compensation value may be a constant value and be predefined or be dependent on the sensed temperature value. Such condensation compensation value may be added to or subtracted from the sensed temperature value. In case no condensation is detected, no action may be required. In another embodiment, the condensation compensation may take the form of a function variable over time that is applied to the values sensed by the temperature sensor in case the condensation indicator indicates the presence of condensation. In such embodiment, the condensation compensation function may in a first time interval lead to the sensed temperature values being reduced, while may in a second time interval following the first time interval lead to the sensed temperature values being increased.

In another embodiment, it is not only condensation that may impact the sensing of the ambient temperature. There may be heat sources in the portable electronic device and/or heat sinks that may make the sensed temperature values deviate from the real ambient temperature values.

In one embodiment, the portable electronic device—which may be a mobile phone or a portable electronic computing device such as a tablet computer in one embodiment—may comprise components that in an active state consume electrical power and thereby release heat, such as a central processing unit or a display. The temperature sensed by the temperature sensor may in this case be impacted by heat migrating from such components to the temperature sensor. This may result in that the temperature sensed by the temperature sensor no longer reflects the real ambient temperature but reflects the real ambient temperature perturbed by the self-heating of the device. Hence, the compensator may additionally be configured for compensating the impact of at least one of the heat releasing electronic components of the device via information being related to the electrical power consumed by this component. A sensed temperature value that is compensated for the impact of one or more heat generating components of the device is referred to as heat compensated temperature value.

The condensation compensation in this case may be applied according to different embodiments: In a first variant, the compensator may be configured to determine the compensated temperature values by applying a condensation compensation function to the heat compensated values in case the condensation indicator indicates the presence of condensation. In this variant, the heat compensation may be applied first, and the condensation compensation may be applied on top of the heat compensation, i.e. to the heat compensated temperature values. Specifically, the condensation compensation function may take the form of a filtering function, and in particular of a filtering function which may filter out condensation evoked fluctuations in the heat compensated temperature values. In a second variant, a thermal model that may be used in the heat compensation may be amended in the event of condensation. Specifically, parameters of the thermal model may be adapted in response to condensation indicated by the condensation indicator. In another variant, a different thermal model of the portable electronic device may be applied in case condensation is detected.

Components of the portable electronic device that may act as heat sources and be compensated for as addressed above may include one or more of a display, a central processing unit, an energy supply such as a battery, a radio frequency transceiver, etc. In a preferred embodiment, the heat compensated temperature value may be determined based on the sensed temperature value and a power consumption related figure of the subject component. For example, in the above embodiment of the display, an intensity of the display may constitute the power related information used for the reason that the brighter the display is operated the more power it consumes. A measure for the intensity of the display, however, may easily be available, e.g. in form of an intensity adjustment setting, while the exact power consumed by the display may be difficult to measure. A load of the central processing unit may be taken as a power related figure therefore, which load in turn may be represented by the number of running processes which is also denoted as CPU utilization, and/or by the number of processes queued in a CPU queue. CPU load data are often supplied by the operating system of the portable electronic device and as such are easily accessible. In another embodiment, the frequency the central processing unit is operated at—which is also denoted as clock rate—may also be taken into account given that the frequency has an impact on the heat generated by the central processing unit. In a preferred embodiment, the load and the frequency contributes to the information for compensating the sensed temperature. For example, the frequency may be multiplied by the load and the result may be input to the compensation model.

For better determining the impact of such power consuming component on the temperature measurement, it is preferred that the heat compensated temperature values may be determined based on a thermal model of the portable electronic device which thermal model in one embodiment indicates a thermal conductivity of one or more heat paths between the one or more components and the temperature sensor. This measure may make the determination of the heat compensated temperature values even more precise since it takes into account the heat flux that effectively arrives at the temperature sensor rather than the bare heat that is generated by the component. In addition, the thermal model may include a thermal capacity of one or more of thermal capacitances in the portable electronic device. Such thermal capacitance may be represented by any element of the portable electronic device being capable of storing thermal energy. For example, a housing of the portable electronic device or parts thereof may be considered as a thermal capacitance. A thermal capacitance does not necessarily consume electrical power but may be heated by components which consume electrical power. The thermal capacitance may store the supplied thermal energy over some time. Such heat may be transferred to the temperature sensor via a thermal conducting path especially when the temperature at the temperature sensor is lower than the temperature of the thermal capacitance.

In another preferred embodiment, a sensed temperature of at least one other temperature sensor arranged in the device may be used for determining the heat compensated temperature values, especially when such temperature sensor is available in the device anyway. Such temperature sensor may include a temperature sensor that is arranged in the portable electronic device for measuring the temperature at a specific location, or the temperature of a specific component, such as, for example, a central processing unit of the device, or a battery.

Preferably, the portable electronic device may be one of a mobile phone, and especially a smart phone, a handheld computer, an electronic reader, a tablet computer, a game controller, a pointing device, a photo or a video camera, a computer peripheral.

In a preferred embodiment, in response to the detection of condensation, one or more of the following actions may be taken: A warning may be given to the user, e.g. on a display of the device; in case the device is a device containing a touchscreen, a sensitivity of the touchscreen may be amended given that it is assumed that the condensate covers the touchscreen. In case of the touchscreen application, it is preferred that a touchscreen controller may receive a signal from the touchscreen and may receive the condensation indicator. The signal received from the touchscreen indicating if a human touches the touch screen may be adapted dependent on the condensation indicator, and in particular may be adapted in case the condensation indicator indicates the presence of condensation, e.g. in order to amplify the signal from the touchscreen in the case of condensation being present. In case the a sensitivity of the touch screen is adjusted in some other way, e.g. in form of a variable, the touchscreen controller may be configured to adapt the sensitivity of the touchscreen dependent on the condensation indicator, and in particular in the case of condensation being present increasing the sensitivity.

In another variant, the condensation indicator may be used for verifying a liquid contact indicator LCI, also referred to as water damage sticker, which may change its colour in response to being in contact with a liquid. This application may even be regarded as independent from the compensation.

According to another aspect of the present invention, a method is provided for operating a portable electronic device. A sensor of the portable electronic device senses an ambient temperature. A dew point is determined, preferably dependent on the sensed temperature. In addition, it is assessed by the portable electronic device if it is exposed to condensation. A corresponding condensation indicator is provided in response to this assessment. The condensation indicator is determined based on the dew point and based on one or more of sensed temperature values of the past or one or more of temperature values derived from the one or more past sensed temperature values.

According to a further aspect of the present invention, a computer program element is provided for operating a portable electronic device, which computer program element, which preferably is stored on a computer storage medium, comprises computer program code means for executing a method according to any of the embodiments of the present invention.

Other advantageous embodiments are listed in the dependent claims as well as in the description below. The described embodiments similarly pertain to the device, the method, and the computer program element. Synergetic effects may arise from different combinations of the embodiments although they might not be described in detail.

Further on it shall be noted that all embodiments of the present invention concerning a method might be carried out in the order of the steps as described. Nevertheless this has not to be the only essential order of steps but all different orders of the method steps shall be comprised in the scope of the claims and be disclosed by the method claims.

BRIEF DESCRIPTION OF THE DRAWINGS

The detailed description refers to embodiments of the present invention. Such description makes reference to the annexed drawings, wherein.

DETAILED DESCRIPTION

Figure 1:
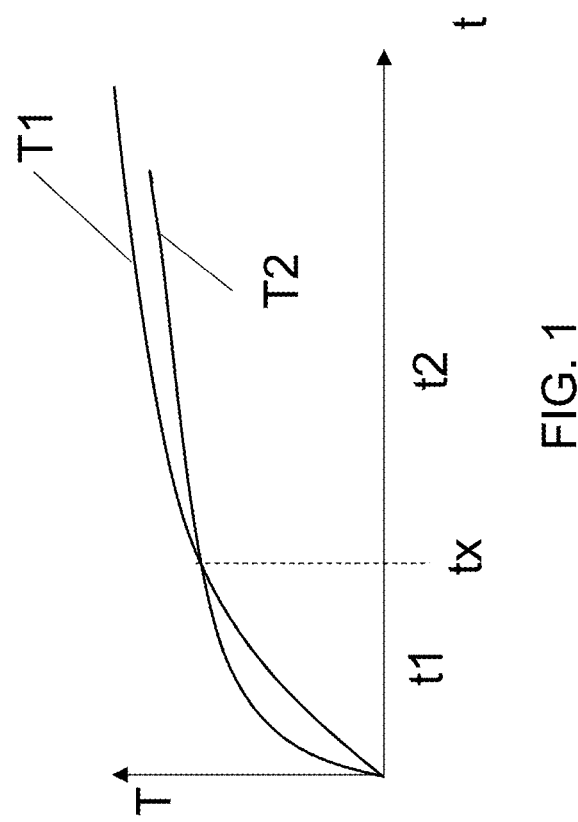
FIG. 1 shows a temperature T over time t chart illustrating the impact of condensation in the sensing of an ambient temperature.

In a temperature T over time t chart according to FIG. 1, the effect of condensation on a temperature measurement is illustrated. The curve T1 denotes the temperature sensed by a temperature sensor in a mobile phone in response to a step change in ambient temperature without the presence of condensation. The curve T2 in contrast denotes the temperature sensed by the temperature sensor in the same mobile phone in response to the step in ambient temperature, however, now with the presence of condensation. During a time interval t1, the temperature values sensed by the temperature sensor are higher in the case of condensation than without, while during a time interval t2 the temperature values sensed by the temperature sensor are lower in the case of condensation than without. The condensate which may appear, for example, as a film of water on the device, conserves latent heat that was previously stored in the water molecules of the humid air. This makes the temperature sensor pretend a temperature higher than real. However, at time tx it is assumed that the condensation reverses into evaporation, wherein the heat stored in the water film is released into the water particles that form the vapor. This has a cooling effect on the device such that the temperature values sensed by the temperature sensor in the interval t2 pretend lower temperature values than real.

Figure 2:
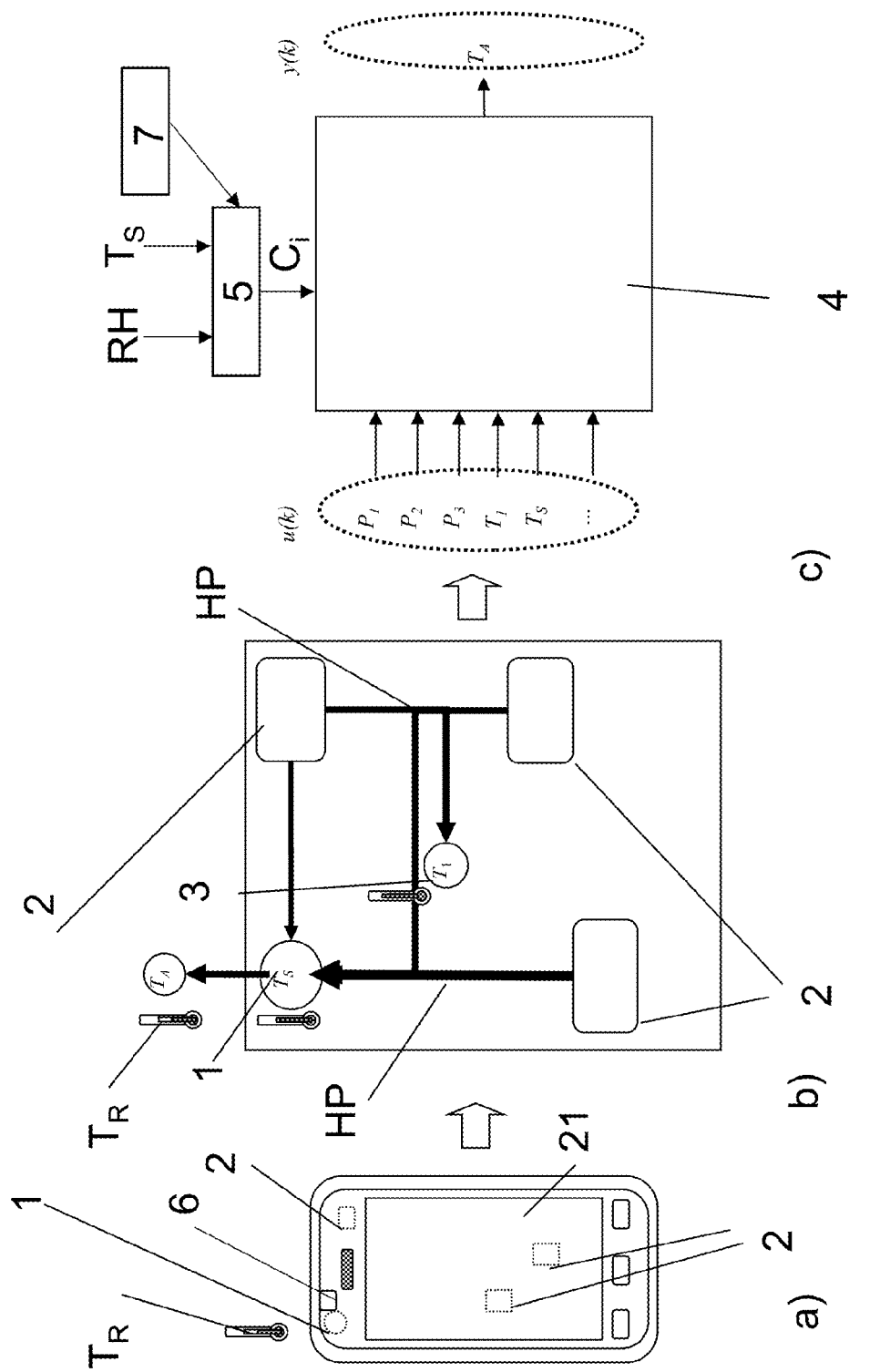
FIG. 2 shows a mobile phone according to an embodiment of the present invention in diagram a), an associated thermal diagram in diagram b), and an associate block diagram in diagram c).

FIG. 2a) shows a diagram illustrating a mobile phone according to an embodiment of the present invention. The mobile phone includes a temperature sensor 1 for sensing an ambient temperature and several components 2 generating heat during operation of the mobile phone, such as a display 21. The temperature sensor 1 provides a sensed temperature value $T_s$ which deviates from a real temperature value $T_R$ of the ambient because of the effect of condensation if present and because of a self-heating of the device that both perturb the temperature sensor 1. Hence, the signal of the integrated temperature sensor 1 is compensated for these effects. The mobile phone further includes a humidity sensor 6.

For determining if condensation occurs, a condensation assessment module 5 is provided in diagram 2c). Preferably, the condensation assessment module 5 receives humidity values RH sensed by the humidity sensor 6 and temperature values $T_s$ sensed by the temperature sensor 1. A dew point temperature may be calculated from these inputs. A storage 7 is provided for storing sensed temperature values of the past. The condensation assessment module 5 may calculate an average sensed temperature value by averaging a number of past sensed temperature values. In the following, the condensation assessment module 5 compares the dew point with the average sensed temperature value. In case the dew point exceeds the average sensed temperature value, condensation shall be detected. A condensation identifier $C_i$ supplies this information to a compensator 4.

In diagram 1b), a "thermal" block diagram of the mobile phone of diagram 1a) is shown in which the heat generating components 2 are connected to the temperature sensor 1 and to each other by heat paths HP on which heat flux is propagated. Preferably, such heat flux propagating to the temperature sensor 1 may be determined and be compensated for at the location of the temperature sensor 1 by the compensator 4, too. The compensator 4 may be an entity represented by hardware, software, or a combination of both and receives the sensed temperature values $T_s$, and possibly sensed inside temperature values $T_1$ from one or more other temperature sensors 3 for sensing a temperature $T_1$ inside the device. Information related to power consumed by one or more of the components 2 may serve as input to the compensator 4, too, such as information $P_1, P_2, P_3$ related to the power consumption of the three components 2 identified as most crucial in impacting the sensed temperature values $T_s$. From all these inputs except for the condensation indicator, heat compensated temperature values are derived over time. The dynamic thermal model of the device may mathematically be described by a differential equation system. The model may in one embodiment comprise one or more, and preferably the most relevant heat sources, and in another embodiment additionally one or more, and preferably the most relevant thermal conductivities, and in another embodiment additionally one or more, and preferably the most relevant heat capacities, as well as it comprises the temperature sensor that is well coupled to the ambient, and it may comprise one or more optional temperature sensors that may be available in the mobile device such as a temperature sensor 3 in diagram 2b) supplying inside temperature values $T_1$. The heat compensated temperature values may then be estimated from these inputs by using the following:

$$x(k+1) = Ax(k) + Bu(k)$$

$$y(k) = Cx(k) + Bu(k) \qquad \text{Collectively Equation 1)}$$

with u(k) denoting the inputs at time step k, y(k) denoting the output $T_A$, and x(k) denoting an internal state vector. A is an n-by-n matrix, B an n-by-m matrix, C an 1-by-n matrix and D an 1-by-m matrix, where n is the number of states that depends on the complexity of the model and m the number of inputs. Typical inputs may be, for example, an intensity of a display, a time derivative of a battery charge level, a central processing unit load, or other power management information. Additional temperature sensors at hot spots of the portable electronic device may improve the compensation results.

Hence, in one embodiment, the portable electronic device is modelled as a thermal system with heat sources, and optionally with heat capacities and/or thermal conductivities. From this model, a time-discrete heat compensator according to the state space description of Equation 1) is derived, that can easily be implemented on a microprocessor of the portable electronic device by using the following software code:
while not stopped

```
{
    u=Read_Input( );      // Read input
    y=C*x+D*u;            // Calculate output
    x=A*x+B*u;            // State Update
    T_HA=y;               // Heat compensated temperature = y
}
```

As a result, the compensator may provide heat compensated temperature values $T_{HA}$. These heat compensated temperature values may then be further compensated in the case of the condensation identifier $C_i$ indicating condensation. For example, a filtering function may be applied to the heat compensated temperature values $T_{HA}$, in order to supply compensated temperature values $T_A$ at the output of the compensator 4, which compensated temperature values $T_A$ in this example are compensated for the impact of heat sources in the device and for the impact of condensation.

The compensated temperature values $T_A$ may be displayed on the display 21 and show the ambient temperature to the user.

While there are shown and described presently preferred embodiments of the invention, it is to be distinctly understood that the invention is not limited thereto but may be otherwise variously embodied and practiced within the scope of the following claims.

The invention claimed is:

1. A portable electronic device, comprising
a temperature sensor for sensing an ambient temperature,
a storage for providing past sensed temperature values and/or past temperature values derived from the past sensed temperature values,
a condensation assessment module for assessing if the portable electronic device is exposed to condensation, and for providing a condensation indicator in response to the assessment,
wherein the condensation assessment module is configured to determine a dew point, and is configured to set the condensation indicator subject to the determined dew point and subject to one or more of the past sensed temperature values or one or more of the past derived temperature values,
further comprising a compensator for compensating for a deviation of a value of the ambient temperature sensed by the temperature sensor from a real value of the ambient temperature, wherein the compensator is configured to determine a compensated temperature value for the ambient temperature at least dependent on the sensed temperature value and dependent on the condensation indicator.

2. A portable electronic device according to claim 1, comprising a humidity sensor,
wherein the condensation assessment module is configured to determine the dew point at least dependent on a humidity value sensed by the humidity sensor and dependent on the sensed temperature value.

3. A portable electronic device according to claim 1,
wherein the condensation assessment module is configured to determine an average or a weighted sensed temperature value based on two or more of the past sensed temperature values, and
wherein the condensation assessment module is configured to set the condensation indicator to a value indicating the presence of condensation if the determined dew point exceeds, or exceeds by at least a defined margin, or exceeds or is equal to the average or the weighted sensed temperature value.

4. A portable electronic device according to claim 1,
wherein the condensation assessment module is configured to set the condensation indicator to a value indicating the presence of condensation if the determined dew point exceeds, or exceeds by at least a defined margin, or exceeds or is equal to one of
one or more of the past sensed temperature values,
one or more of the past derived temperature values if any.

5. A portable electronic device according to claim 1,
wherein the condensation assessment module is configured to determine an average or a weighted derived temperature value based on two or more of the past derived temperature values, and
wherein the condensation assessment module is configured to set the condensation indicator to a value indicating the presence of condensation if the determined dew point exceeds, or exceeds by at least a defined margin, or exceeds or is equal to the average or the weighted derived temperature value.

6. A portable electronic device according to claim 1,
wherein the condensation indicator is a binary indicator indicating either a presence of condensation or an absence of condensation.

7. A portable electronic device according to claim 1,
wherein the compensator is configured to determine the compensated temperature value by applying a condensation compensation value to the sensed temperature value in case the condensation indicator indicates the presence of condensation.

8. A portable electronic device according to claim 1,
wherein the compensator is configured to determine compensated temperature values by applying a condensation compensation function over time to the temperature values sensed by the temperature sensor in case the condensation indicator indicates the presence of condensation.

9. A portable electronic device according to claim 1,
comprising a humidity sensor,
wherein the condensation assessment module is configured to determine the dew point at least dependent on a humidity value sensed by the humidity sensor and dependent on the compensated temperature value.

10. A portable electronic device according to claim 1,
wherein the storage is configured to provide past compensated temperature values as past derived temperature values, and
wherein the condensation assessment module is configured to set the condensation indicator to a value indicating the presence of condensation if the determined dew point exceeds, or exceeds by at least a defined margin, or exceeds or is equal to one or more of the past compensated temperature values.

11. A portable electronic device according to claim 1,
wherein the storage is configured to provide past compensated temperature values as past derived temperature values,
wherein the condensation assessment module is configured to determine an average or a weighted compensated temperature value based on two or more of the past compensated temperature values, and
wherein the condensation assessment module is configured to set the condensation indicator to a value indicating the presence of condensation if the determined dew point exceeds, or exceeds by at least a defined margin, or exceeds or is equal to the average or weighted compensated temperature value.

12. A portable electronic device according to claim 11,
comprising a set of components radiating heat in response to the consumption of electrical energy,
wherein the thermal model is configured to determine a heat propagation as a function of time from at least one of the components of the set to the temperature sensor,
wherein the compensator is configured to determine the heat compensated temperature value dependent on the sensed temperature value, dependent on information related to electrical power consumed by at least one component of the set, and based on the thermal model.

13. A portable electronic device according to claim 11,
comprising at least one other temperature sensor for sensing a temperature inside the portable electronic device,
wherein the compensator is configured to determine the heat compensated temperature value in addition dependent on the one or more temperature values sensed by the at least one other temperature sensor.

14. A portable electronic device according to claim 1,
wherein the compensator comprises a thermal model of the portable electronic device for modelling the impact of one or more heat sources and/or one or more heat sinks of the portable electronic device on the temperature values sensed by the temperature sensor,
wherein the compensator is configured to determine a heat compensated temperature value dependent on the sensed temperature value and by means of the thermal model, and
wherein the compensator is configured to determine the compensated temperature value by applying a condensation compensation value to the heat compensated temperature value in case the condensation indicator indicates the presence of condensation.

15. A portable electronic device according to claim 14,
wherein the compensator is configured to determine the compensated temperature values by applying a condensation compensation function to the heat compensated values in case the condensation indicator indicates the presence of condensation, in particular wherein the condensation compensation function is a filtering function.

16. A portable electronic device according to claim 14,
wherein the compensator is configured to adapt one or more parameters of the thermal model of the portable electronic device in case the condensation indicator indicates the presence of condensation.

17. A portable electronic device according to claim 1,
wherein the compensator is configured to apply a different thermal model of the portable electronic device in case the condensation indicator indicates a presence of condensation.

18. A portable electronic device according to claim 1, comprising
a touchscreen, and
a touchscreen controller configured to one or more of
adapting a signal received from the touchscreen dependent on the condensation indicator, and in particular adapting the signal received from the touchscreen in case the condensation indicator indicates the presence of condensation,
adapting a sensitivity of the touch screen dependent on the condensation indicator, and in particular adapting the sensitivity of the touchscreen in case the condensation indicator indicates the presence of condensation.

19. A method for operating a portable electronic device, comprising
sensing an ambient temperature of the portable electronic device by means of a temperature sensor,
determining a dew point,
setting a condensation indicator subject to the determined dew point and subject to one or more of past sensed temperature values or to one or more of temperature values derived from the one or more past sensed temperature values, and
compensating for a deviation of a value of the ambient temperature sensed by the temperature sensor from a real value of the ambient temperature, using a compensator configured to determine a compensated temperature value for the ambient temperature at least dependent on the sensed temperature value and dependent on the condensation indicator.

20. A non-transitory computer program element for operating a portable electronic device, comprising computer program code means for implementing a method according to claim 19 when executed on a central processing unit of the portable electronic device.

* * * * *